(12) United States Patent
Masai et al.

(10) Patent No.: US 7,321,035 B2
(45) Date of Patent: Jan. 22, 2008

(54) PROCESS FOR PRODUCING 2,6-DIHALOGENOPURINE

(75) Inventors: Naruhito Masai, Osaka (JP); Taketo Hayashi, Osaka (JP); Hiroharu Kumazawa, Osaka (JP); Junichi Nishikawa, Osaka (JP); Istvan Barta, Paty (HU); Takehiko Kawakami, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 461 days.

(21) Appl. No.: 10/991,505

(22) Filed: Nov. 19, 2004

(65) Prior Publication Data

US 2005/0090666 A1    Apr. 28, 2005

Related U.S. Application Data

(62) Division of application No. 10/296,234, filed as application No. PCT/JP02/03325 on Apr. 3, 2002, now Pat. No. 6,936,713.

(30) Foreign Application Priority Data

Apr. 5, 2001    (JP) .............................. 2001-107004

(51) Int. Cl.
    *C07D 473/40*    (2006.01)
(52) U.S. Cl. ...................................... 544/277
(58) Field of Classification Search ................ 544/277
    See application file for complete search history.

(56) References Cited

U.S. PATENT DOCUMENTS

| 3,314,938 | A | 4/1967 | Kawashima et al. | |
|---|---|---|---|---|
| 6,093,819 | A | 7/2000 | Hanson | |
| 6,455,696 | B2 | 9/2002 | Hayashi et al. | |
| 2004/0102459 | A1* | 5/2004 | Gillespie et al. | 514/263.2 |
| 2005/0131229 | A1* | 6/2005 | Hayashi et al. | 544/264 |

FOREIGN PATENT DOCUMENTS

| EP | 138683 | 4/1985 |
|---|---|---|
| EP | 0 433 845 A1 | 6/1991 |
| EP | 1172365 | 1/2002 |
| IE | 904517 | 6/1991 |
| JP | 6-92965 | 4/1994 |

OTHER PUBLICATIONS

Nathanael S. Gray et al.: "Combinational synthesis of 2, 9-substituted purines" Tetrahedron Letter, vol. 38, No. 7, pp. 1161-1164, 1997.

J. Warren Beach et al.: "A highly stereoselective synthesis of anti-HIV 2', 3'-dideoxy- and 2', 3'-didehydro-2', 3'-dideoxynucleosides" J. Org. Chem., vol. 57, No. 14, pp. 3887-3894, 1992.

Suzanne E. Keeling et al.: "The discovery and synthesis of highly potent, $A_{2a}$ receptor agonists" Bioorganic & Medicinal Chemistry Letters, vol. 10, pp. 403-406, 2000.

Kazunori Niiya et al.: "2-(N'-alkylidenehydrazino) adenosines: Potent and selective coronary vasodilators" J. Med. Chem., vol. 35, No. 24, pp. 4557-4561, 1992.

B. Ha Seung et al.: "New base-altered adenosine analogues: synthesis and affinity at adenosine $A_1$ and $A_{2A}$ receptors" Bioorganic & Medicinal Chemistry Letters, vol. 7, No. 24, pp. 3085-3090, Jan. 16, 2002.

Elizabeth Dyer et al.: "Acylations of some 2-amino-6-halo- and 2-amino-6-alkylthiopurines" J. Med. Chem., vol. 11, No. 6, pp. 1232-1234, 1968.

Radiochimiya, vol. 23, No. 4, pp. 607-613, 1981, with English translation.

Michael R. Harnden et al.: "Analogues of the antiviral acyclonucleoside 9-(4-hydroxy-3-hydroxymethylbutyl)guanine. Part 4. Substitution on the 2-amino group" J. Chem. Soc., Perkins Trans. 1, pp. 2207-2213, 1989.

Anupma Dhanda et. al.: "Facile conversion of 4-endo-hydroxy-2-oxablcyclo[3.3.0]oct-7-en-3-one into carbocyclic 2'-deoxyribonucleoside analogues" J. Chem. Soc., Perkins Trans. 1, pp. 3469-3475, 1999.

Vasu Nair, et al., "Modification of Nucleic Acid Bases Via Radical Intermediates: Synthesis Of Dihalogenated Purine Nucleosides," Synthesis, vol. 8, 1982, pp. 670-672.

P. Francom, et al., "Nucleic Acid Related Compounds 116. Nonaqueous Diazotization of Aminopurine Nucleosides." Journal of Organic Chemistry, vol. 67, No. 19, 2002, pp. 6788-6796.

Richard E. Austin, Tet. Letters 43 6169 (2002).

Robert H. Iwamoto, et al., 2'-Deoxythioguanosine And Related Nucleosides, Journal Of Medicinal Chemistry, vol. 6, pp. 684-688, 1963.

* cited by examiner

*Primary Examiner*—Mark L. Berch
(74) *Attorney, Agent, or Firm*—Oblon, Spivak, McClelland, Maier & Neustadt, P.C.

(57) ABSTRACT

A process for conveniently and efficiently preparing a 2,6-dihalogenopurine using an inexpensive starting material. A process for preparing a 2,6-dihalogenopurine, comprising treating a 2-amino-6-halogenopurine having a protective group at $7^{th}$ position or $9^{th}$ position with a diazotizating agent and a halogen source; and a process for preparing a 9-acyl-2-amino-6-halogenopurine, comprising treating a 2-amino-6-halogenopurine with an acylating agent in the presence of a base.

16 Claims, No Drawings

PROCESS FOR PRODUCING 2,6-DIHALOGENOPURINE

CROSS REFERENCES TO RELATED APPLICATIONS

This application is a divisional application of U.S. patent application Ser. No. 10/296,234, filed on Dec. 4, 2002 now U.S. Pat. No. 6,936,713 and now allowed, which is a national stage application of PCT/JP02/03325, filed on Apr. 3, 2002, and claims priority to Japanese Patent Application No. 2001-107004, filed on May 4, 2001, all of which are incorporated herein by reference in their entireties.

TECHNICAL FIELD

The present invention relates to a process for preparing a 2,6-dihalogenopurine. More specifically, the present invention relates to a process for preparing 2,6-dihalogenopurine which is useful as a raw material for nucleoside analogues which are useful as pharmaceuticals. BACKGROUND ART As a process for preparing a 2,6-dihalogenopurine, there have been known, for instance, (A) a process comprising chlorinating xanthine with pyrophosphoryl chloride [*J. Am. Chem. Soc.* 78, 3508-10 (1956)]; (B) a process comprising chlorinating hypoxanthine or N-oxide of 6-chloropurine with phosphorus oxychloride (Japanese Examined Patent Publication No. Sho 45-11508 and U.S. Pat. No. 3,314,938); (C) a process comprising four steps using a barbituric acid derivative as a starting material [*J. Org. Chem.* 19, 930 (1954) and *J. Am. Chem. Soc.* 80, 404-8 (1958)]; (D) a process comprising cyclizing 2,4-dichloro-5,6-diaminopyridine (U.S. Pat. No. 2,844,576); and the like.

However, there are some defects in the above-mentioned process (A) that there is a necessity to prepare pyrophosphoryl chloride as a halogenating agent from phosphorus oxychloride in a complicated method, that a high reaction temperature of 165° C. is required, that a corrosion-resistant reaction vessel is necessitated during the reaction, and that a long period of time of about 19 hours is required for the reaction.

In addition, there are some defects in all of the above-mentioned processes (A) to (D) that their preparation steps are so long, thereby requiring complicated procedures.

DISCLOSURE OF INVENTION

The present invention has been accomplished in view of the prior art described above, and its object is to provide a process capable of conveniently and efficiently preparing a 2,6-dihalogenopurine by using an inexpensive starting material.

The present invention relates to:
(1) a process for preparing a 2,6-dihalogenopurine, comprising treating a 2-amino-6-halogenopurine having a protective group at 7th position or 9th position with a diazotizating agent and a halogen source; and
(2) a process for preparing a 9-acyl-2-amino-6-halogenopurine, comprising treating a 2-amino-6-halogenopurine with an acylating agent in the presence of a base.

BEST MODE FOR CARRYING OUT THE INVENTION

According to the present invention, a 2,6-dihalogenopurine is obtained by treating a 2-amino-6-halogenopurine having a protective group at 7th position or 9th position with a diazotizating agent and a halogen source.

The 2-amino-6-halogenopurine having a protective group at 7th position or 9th position can be obtained by using a 2-amino-6-halogenopurine as a starting material, and introducing a protective group into the 7th position or 9th position of the 2-amino-6-halogenopurine. The 2-amino-6-halogenopurine has been industrially prepared, and is readily available.

The protective group of the 2-amino-6-halogenopurine having a protective group at 7th position or 9th position includes an acyl group, a carbamoyl group, and the like. Among them, the acyl group is preferable.

Concrete examples of the acyl group include an acyl group having 2 to 7 carbon atoms, which may be branched or have a substituent, such as acetyl group, propionyl group, butanoyl group and benzoyl group; and the like. Concrete examples of the carbamoyl group include a carbamoyl group having 2 to 7 carbon atoms, which may be branched or have a substituent. The above-mentioned substituents include, for instance, phenyl group and the like. Among these protective groups, acetyl group is preferable from the viewpoint of improvement in reactivity and economics.

The process for introducing a protective group into the 7th position or 9th position of the 2-amino-6-halogenopurine includes, for instance, a process comprising treating a 2-amino-6-halogenopurine with a reagent for introducing a protective group in the presence of a base.

When an acid anhydride is used as the reagent for introducing a protective group, the protective group can be introduced into the 7th position or 9th position of the 2-amino-6-halogenopurine without using a base.

The base includes an organic base such as triethylamine, an inorganic base such as a carbonate and a hydrogencarbonate, and the like. Among them, triethylamine is preferable from the viewpoint of improvement in reactivity.

It is desired that the amount of the base is usually 1 to 3 mol, preferably 1.5 to 2 mol, per 1 mol of the 2-amino-6-halogenopurine from the viewpoint of improvement in reactivity and economics.

The reagent for introducing a protective group includes, for instance, an acylating agent having 2 to 7 carbon atoms, such as acetic anhydride, an acetyl halide, propionic anhydride, a propionyl halide, butyric anhydride and a butyryl halide; a carbamoylation agent having 2 to 7 carbon atoms, such as di-t-butyl dicarbonate and a halogenated t-butyl carbonate; and the like. Among them, the acylating agent is preferable, and acetic anhydride and the acetyl halide are more preferable, and acetic anhydride is still more preferable.

It is desired that the amount of the reagent for introducing a protective group is usually 1 to 3 mol, preferably 1.1 to 2 mol per 1 mol of the 2-amino-6-halogenopurine.

The protective group can be introduced into the 7th position or 9th position of the 2-amino-6-halogenopurine by, for instance, mixing given amounts of the 2-amino-6-halogenopurine, the base and the reagent for introducing a protective group, and heating the resulting mixture with stirring. The reaction temperature may be usually 1° to 100° C. or so. Also, the reaction time can be up to the introduction of the protective group into the 7th position or 9th position of the 2-amino-6-halogenopurine. The reaction time is usually 1 to several hours or so. The introduction of the protective group into the 7th position or 9th position of the 2-amino-6-halogenopurine can be readily confirmed by high-performance liquid chromatography (HPLC).

After the termination of the reaction, it is preferable that the temperature of the resulting reaction mixture is adjusted to 10° to 30° C., and an organic solvent is added thereto to dilute the solution. The organic solvent includes, for instance, hydrocarbon-based, alcohol-based, ester-based, or ether-based organic solvent and the like. The amount of the organic solvent is not limited to specified ones, and is usually 100 to 500 parts by weight or so, based on 100 parts by weight of the 2-amino-6-halogenopurine having a protective group.

The 2-amino-6-halogenopurine having a protective group at 7th position or 9th position is contained in the resulting reaction solution, and this 2-amino-6-halogenopurine having a protective group at 7th position or 9th position can be collected by filtration. The collected 2-amino-6-halogenopurine having a protective group at 7th position or 9th position may be purified as occasion demands.

Thus, the 2-amino-6-halogenopurine having a protective group at 7th position or 9th position can be obtained.

When the 2-amino-6-halogenopurine is acetylated in an organic solvent such as N,N-dimethylacetamide in the presence of acetic anhydride, a 2,6-dihalogenopurine can be obtained by treating the formed 2-amino-6-halogenopurine having a protective group at 7th position or 9th position with a diazotizating agent such as isoamyl nitrite, and a halogen source such as thionyl chloride or lithium chloride, without the isolation from the reaction solution.

Representative examples of the 2-amino-6-halogenopurine having a protective group at 7th position include a 7-acyl-2-amino-6-chloropurine having an acyl group of 2 to 7 carbon atoms, which may be branched or have a substituent; a 7-carbamoyl-2-amino-6-chloropurine having a carbamoyl group of 2 to 7 carbon atoms, which may be branched or have a substituent; a 7-acyl-2-amino-6-bromopurine having an acyl group of 2 to 7 carbon atoms, which may be branched or have a substituent; a 7-carbamoyl-2-amino-6-bromopurine having a carbamoyl group of 2 to 7 carbon atoms, which may be branched or have a substituent; a 7-acyl-2-amino-6-iodopurine having an acyl group of 2 to 7 carbon atoms, which may be branched or have a substituent; a 7-carbamoyl-2-amino-6-iodopurine having a carbamoyl group of 2 to 7 carbon atoms, which may be branched or have a substituent; a 7-acyl-2-amino-6-fluoropurine having an acyl group of 2 to 7 carbon atoms, which may be branched or have a substituent; a 7-carbamoyl-2-amino-6-fluoropurine having a carbamoyl group of 2 to 7 carbon atoms, which may be branched or have a substituent; and the like.

Representative examples of the 2-amino-6-halogenopurine having a protective group at 9th position include a 9-acyl-2-amino-6-chloropurine having an acyl group of 2 to 7 carbon atoms, which may be branched or have a substituent; a 9-carbamoyl-2-amino-6-chloropurine having a carbamoyl group of 2 to 7 carbon atoms, which may be branched or have a substituent; a 9-acyl-2-amino-6-bromopurine having an acyl group of 2 to 7 carbon atoms, which may be branched or have a substituent; a 9-carbamoyl-2-amino-6-bromopurine having a carbamoyl group of 2 to 7 carbon atoms, which may be branched or have a substituent; a 9-acyl-2-amino-6-iodopurine having an acyl group of 2 to 7 carbon atoms, which may be branched or have a substituent; a 9-carbamoyl-2-amino-6-iodopurine having a carbamoyl group of 2 to 7 carbon atoms, which may be branched or have a substituent; a 9-acyl-2-amino-6-fluoropurine having an acyl group of 2 to 7 carbon atoms, which may be branched or have a substituent; a 9-carbamoyl-2-amino-6-fluoropurine having a carbamoyl group of 2 to 7 carbon atoms, which may be branched or have a substituent; and the like.

Among the 2-amino-6-halogenopurines having a protective group at 7th position or 9th position, the 9-acyl-2-amino-6-chloropurine is preferable, and 9-acetyl-2-amino-6-chloropurine is more preferable.

Next, a 2,6-dihalogenopurine can be obtained by treating the 2-amino-6-halogenopurine having a protective group at 7th position or 9th position with a diazotizating agent and a halogen source.

The diazotizating agent includes nitrites such as sodium nitrite and potassium nitrite, an ester of nitrous acid, nitrosyl chloride, nitrosylsulfuric acid, nitrogen monoxide, and the like. Among them, the ester of nitrous acid is preferable from the viewpoint of improvement in reactivity and yield.

The ester of nitrous acid includes isoamyl nitrite, isobutyl nitrite, ethyl nitrite, propyl nitrite, isopropyl nitrite, butyl nitrite, tert-butyl nitrite, amyl nitrite, and the like.

Among the esters of nitrous acid, isoamyl nitrite, isobutyl nitrite and tert-butyl nitrite are preferable, and isoamyl nitrite is more preferable, from the viewpoint of improvement in reactivity and suppression of the formation of by-products.

It is desired that the amount of the diazotizating agent is usually 1 to 3 mol, preferably 1.1 to 2 mol per 1 mol of the 2-amino-6-halogenopurine having a protective group at 7th position or 9th position from the viewpoint of improvement in reactivity and economics.

The halogen source includes metal halides and nonmetal halides, and these can be used alone or in admixture.

The metal halide includes, for instance, metal chlorides, metal bromides, and the like.

The metal chloride includes lithium chloride, potassium chloride, sodium chloride, calcium chloride, magnesium chloride, zinc chloride, nickel chloride, cuprous chloride, cupric chloride, and the like. Among them, lithium chloride is preferable from the viewpoint of improvement in reactivity and yield.

The metal bromide includes lithium bromide, potassium bromide, sodium bromide, calcium bromide, magnesium bromide, zinc bromide, nickel bromide, cuprous bromide, cupric bromide, and the like.

The nonmetal halide includes chlorinating agents, brominating agents, fluorine-containing compounds, and the like.

The chlorinating agent includes chlorine, hydrochloric acid, hydrogen chloride, thionyl chloride, sulfuryl chloride, mesyl chloride, phosphorus oxychloride, phosphorus trichloride, phosphorus pentachloride, N-chlorosuccinimide, and the like. Among them, thionyl chloride is preferable from the viewpoint of improvement in reactivity and yield.

The brominating agent includes bromine, hydrobromic acid, hydrogen bromide, thionyl bromide, phosphorus oxybromide, phosphorus tribromide, phosphorus pentabromide, N-bromosuccinimide, and the like.

The fluorine-containing compound includes a boron trifluoride complex, hydrogen fluoride, and the like. The boron trifluoride complex includes boron trifluoride diethyl ether complex, boron trifluoride tetrahydrofuran complex, and the like.

In the present invention, the combination of a metal halide and a nonmetal halide is preferable from the viewpoint of improvement in reactivity and yield. Among them, it is especially preferable to use lithium chloride as the metal halide and thionyl chloride as the nonmetal halide, from the viewpoint of improvement in reactivity and yield, and suppression of the formation of by-products.

When the metal halide and the nonmetal halide are used in combination, the ratio of the metal halide to the nonmetal halide (metal halide/nonmetal halide:molar ratio) is preferably 1/1 to 10/1, more preferably 2/1 to 6/1, from the viewpoint of improvement in reactivity, yield and economics, and suppression of the formation of by-products.

Also, in the present invention, the above-mentioned metal halide and an acid may be used in combination. In this case, it is preferable to use an acid such as p-toluenesulfonic acid, methanesulfonic acid, trifluoromethanesulfonic acid, trichloroacetic acid, trifluoroacetic acid, acetic acid, propionic acid, formic acid or sulfuric acid.

When the metal halide and the acid are used in combination, the ratio of the metal halide to the acid (metal halide/acid:molar ratio) is preferably 1/1 to 10/1, more preferably 2/1 to 6/1 from the viewpoint of improvement in reactivity, yield and economics, and suppression of the formation of by-products.

It is desired that the amount of the halogen source is usually 1 to 3 mol, preferably 1.0 to 1.5 mol per 1 mol of the 2-amino-6-halogenopurine having a protective group at 7th position or 9th position from the viewpoint of improvement in reactivity, suppression of the formation of by-products and the increase in economics.

When the 2-amino-6-halogenopurine having a protective group at 7th position or 9th position is treated with a diazotizating agent and a halogen source, a reaction solvent can be used.

As the reaction solvent, an organic solvent can be favorably used.

The organic solvent includes, for instance, polar solvents such as tetrahydrofuran, acetonitrile, N,N-dimethylformamide, N,N-dimethylacetamide, N-methylpyrrolidone, dimethyl sulfoxide and 1,2-dimethoxyethane; organic acids such as acetic acid, propionic acid and formic acid; and the like. Among them, N,N-dimethylacetamide, N,N-dimethylformamide and tetrahydrofuran are preferable, and N,N-dimethylacetamide is more preferable from the viewpoint of improvement in reactivity and yield, and suppression of the formation of by-products.

The amount of the reaction solvent is not limited to specified ones. It is desired that the amount is usually 100 to 2000 parts by weight, preferably 500 to 1000 parts by weight based on 100 parts by weight of the 2-amino-6-halogenopurine having a protective group at 7th position or 9th position.

Thus, a suspension of the 2-amino-6-halogenopurine having a protective group at 7th position or 9th position is obtained by adding the metal halide and the 2-amino-6-halogenopurine having a protective group at 7th position or 9th position to the reaction solvent.

When the halogenating agent is used as a halogen source, the halogenating agent and the diazotizating agent are added to the suspension of the 2-amino-6-halogenopurine having a protective group at 7th position or 9th position. The liquid temperature of the suspension during the addition cannot be absolutely determined because the liquid temperature differs depending upon the kinds of the halogen source and the diazotizating agent, and the like. It is preferable that the liquid temperature is −10° to 80° C. or so from the viewpoint of improvement in reactivity and suppression of the formation of by-products.

In the reaction solution thus obtained, the formed 2,6-dihalogenopurine having a protective group at 7th position or 9th position is contained.

The protective group of the 2,6-dihalogenopurine can be deprotected by adding water to the reaction solution. The deprotection of the protective group is carried out in a weakly acidic solution, for instance, at the pH of 3 to 7. When the reaction solution is strongly acidic, its pH may be adjusted to 3 to 7 by adding an inorganic base such as a hydrogencarbonate or a carbonate, or an organic base such as triethylamine.

The formed 2,6-dihalogenopurine can be collected by subjecting the resulting solution to an after-treatment by a conventional method.

For instance, the formed 2,6-dihalogenopurine can be collected as crystals by extracting the formed 2,6-dihalogenopurine from the reaction solution with acetonitrile, ethyl acetate, methyl isobutyl ketone or the like, and thereafter concentrating the extract. Alternatively, the formed 2,6-dihalogenopurine can be collected by adding to the extract, for instance, a basic aqueous solution such as aqueous sodium hydroxide to extract the 2,6-dihalogenopurine, adding an acid such as hydrochloric acid thereto to neutralize the aqueous solution, and filtering the precipitated 2,6-halogenopurine crystal. Thereafter, the 2,6-halogenopurine may be purified and dried by a conventional method.

Thus, according to the present invention, a desired compound 2,6-dihalogenopurine can be conveniently and efficiently prepared by using an inexpensive 2-amino-6-halogenopurine having a protective group at 7th position or 9th position as a starting material.

The present invention will be more specifically described on the basis of the following examples, without intending to limit the present invention thereto.

EXAMPLE 1

Preparation of 9-Acetyl-2-amino-6-chloropurine

A mixture of 204.2 g (2.00 mol) of acetic anhydride, 202.4 g (2.00 mol) of triethylamine and 169.6 g (1.00 mol) of 2-amino-6-chloropurine was stirred at 80° C. for 1 hour. The resulting suspension was cooled at 25° C., and thereafter diluted with 400 mL of toluene, and the diluted solution was filtered. The resulting crystals were suspended in 300 mL of isopropanol, and the suspension was filtered again. The resulting crystals were dried at 60° C. under reduced pressure, to give 211.8 g of white powder of 9-acetyl-2-amino-6-chloropurine (yield 100%).

[Physical Properties of the Resulting 9-acetyl-2-amino-6-chloropurine]

$^1$H-NMR (400 MHz, DMSO-$d_6$): δ(ppm)=2.83 (s, 3H), 7.26 (br, s, 2H), 8.55 (s, 1H)

$^{13}$C-NMR (100 MHz, DMSO-$d_6$): δ(ppm)=24.6, 124.0, 139.7, 150.1, 152.9, 160.1, 167.7

EXAMPLE 2

Preparation of 2,6-Dichloropurine

In 160.0 g of N,N-dimethylacetamide was dissolved 16.0 g (0.377 mol) of lithium chloride. Thereafter, the mixture was cooled to 30° C., and 20.0 g (0.095 mol) of 9-acetyl-2-amino-6-chloropurine was added thereto. To the resulting suspension was added 11.8 g (0.099 mol) of thionyl chloride together with 16.6 g (0.14 mol) of isoamyl nitrite at a temperature of at most 10° C. over a period of 1 hour. After the addition, the mixture was stirred at room temperature for 3 hours.

After the termination of the reaction, 16.0 g of sodium hydrogencarbonate and 160 g of water were added to the reaction solution. The reaction solution was analyzed by high-performance liquid chromatography. As a result, it was found that 15.0 g of 2,6-dichloropurine was contained in the reaction solution. The reaction yield was 84.0%.

The reaction solution was extracted five times with 150 mL of ethyl acetate. The extracts were combined, and thereafter extracted again twice with 30 g of a 4N-aqueous sodium hydroxide and extracted once with 30 g of a 2N-aqueous sodium hydroxide. The resulting alkali extracts were combined, and thereafter the pH was adjusted to 5 with a 35% hydrochloric acid to precipitate crystals under acidic conditions. After the filtration, the resulting crystals were dried at 60° C. under reduced pressure, to give 12.6 g of pale yellowish powder of 2,6-dichloropurine (yield: 70.5%).

[Physical Properties of the Resulting 2,6-dichloropurine]

Melting point: 188°-190° C. (literature value: 188°-190° C.)

$^1$H-NMR (400 MHz, DMSO-$d_6$): δ(ppm)=8.74 (s, 1H), 14.15 (s, 1H)

$^{13}$C-NMR (100 MHz, DMSO-$d_6$): δ(ppm)=128.3, 147.2, 150.6, 155.9

EXAMPLE 3

The same procedures up to the analysis of the reaction solution as in Example 2 were carried out by using 14.4 g (0.14 mol) isobutyl nitrite in place of 16.6 g (0.14 mol) isoamyl nitrite used in Example 2.

The reaction solution was analyzed. As a result, the reaction yield of the resulting 2,6-dichloropurine was 79.6%.

EXAMPLE 4

The same procedures up to the analysis of the reaction solution as in Example 2 were carried out by using 14.4 g (0.14 mol) tert-butyl nitrite in place of 16.6 g (0.14 mol) isoamyl nitrite used in Example 2.

The reaction solution was analyzed. As a result, the reaction yield of the resulting 2,6-dichloropurine was 70.1%.

EXAMPLE 5

The same procedures up to the analysis of the reaction solution as in Example 2 were carried out by using 13.4 g (0.099 mol) of sulfuryl chloride in place of 11.8 g (0.099 mol) of thionyl chloride used in Example 2.

The reaction solution was analyzed. As a result, the reaction yield of the resulting 2,6-dichloropurine was 73.7%.

EXAMPLE 6

The same procedures up to the analysis of the reaction solution as in Example 2 were carried out by using 15.2 g (0.099 mol) of phosphorus oxychloride in place of 11.8 g (0.099 mol) of thionyl chloride used in Example 2.

The reaction solution was analyzed. As a result, the reaction yield of the resulting 2,6-dichloropurine was 65.2%.

EXAMPLE 7

The same procedures up to the analysis of the reaction solution as in Example 2 were carried out by using 160.0 g of N,N-dimethylformamide in place of 160.0 g of N,N-dimethylacetamide used in Example 2.

The reaction solution was analyzed. As a result, the reaction yield of the resulting 2,6-dichloropurine was 68.3%.

EXAMPLE 8

The same procedures up to the analysis of the reaction solution as in Example 2 were carried out by using 160.0 g of tetrahydrofuran in place of 160.0 g of N,N-dimethylacetamide used in Example 2.

The reaction solution was analyzed. As a result, the reaction yield of the resulting 2,6-dichloropurine was 56.0%.

EXAMPLE 9

To 100 mL of N,N-dimethylacetamide were added 10.0 g (0.236 mol) of lithium chloride, 10.0 g (0.059 mol) of 2-amino-6-chloropurine and 7.2 g (0.071 mol) of acetic anhydride, with stirring. The temperature of the resulting suspension was raised to 45° to 50° C., and stirred for 45 minutes. The resulting reaction solution was cooled to at most 10° C., and 7.4 g (0.062 mol) of thionyl chloride was added together with 10.4 g (0.089 mol) of isoamyl nitrite to the reaction mixture over a period of 1 hour. After the addition, the mixture was stirred at a temperature of at most 15° C. for 17 hours.

The reaction solution was analyzed. As a result, the reaction yield of the resulting 2,6-dichloropurine was 76.6%.

EXAMPLE 10

The amount 1.00 g (4.72 mmol) of 9-acetyl-2-amino-6-chloropurine and 1.00 g (7.02 mmol) of boron trifluoride-diethyl ether complex were mixed with 25 mL of tetrahydrofuran. The resulting mixture was heated to 45° to 50° C., and 1.10 g (9.39 mmol) of isoamyl nitrite was added thereto in a thin stream. After the termination of the addition in a thin stream, the solution was stirred for additional one hour. Thereafter, 50 mL of water was added to the solution, and the mixture was extracted with methyl isobutyl ketone (50 mL, thrice). The organic solvent was distilled under reduced pressure, and the resulting residue was purified by silica gel chromatography, to give 0.39 g (2.26 mmol) of 2-fluoro-6-chloropurine (yield: 48%).

$^1$H-NMR (DMSO-$d_6$): 8.69 (s, 1H)

$^{13}$C-NMR (DMSO-$d_6$): 128.0, 147.4, 148.4, 155.0, 157.1

MS (EI) m/z 174 (M$^+$, 35), 172 (M$^+$, 100), 137 (43)

EXAMPLE 11

The same procedures as in Example 10 were carried out except that 6 mL of a 12% hydrogen fluoride-1,2-dimethoxyethane solution was used in place of the boron trifluoride-diethyl ether complex used in Example 10, and that the reaction temperature was changed to −10° C., to give 2-fluoro-6-chloropurine.

EXAMPLE 12

The same procedures up to the analysis of the reaction solution as in Example 2 were carried out by using 9.5 g (0.099 mol) of methanesulfonic acid in place of 11.8 g (0.099 mol) of thionyl chloride used in Example 2. The reaction solution was analyzed. As a result, the reaction yield of the resulting 2,6-dichloropurine was 68.5%.

EXAMPLE 13

The same procedures up to the analysis of the reaction solution as in Example 2 were carried out by using 4.9 g (0.050 mol) of sulfuric acid in place of 11.8 g (0.099 mol) of thionyl chloride used in Example 2. The reaction solution was analyzed. As a result, the reaction yield of the resulting 2,6-dichloropurine was 71.6%.

INDUSTRIAL APPLICABILITY

According to the process of the present invention, there can be conveniently and efficiently prepared a 2,6-dihalogenopurine by using an inexpensive starting material. The resulting 2,6-dihalogenopurine can be suitably used in the preparation of nucleoside derivatives described in *J. Org. Chem.* 57, 3887-3894 (1992).

The invention claimed is:

1. A process for preparing a 9-acetyl-2-amino-6-halogenopurine, comprising treating a 2-amino-6-halogenopurine with an acetylating agent in the presence of a base.

2. The process according to claim 1, wherein the base is triethylamine.

3. The process according to claim 1, wherein the acetylating agent is acetic anhydride.

4. The process according to claim 2, wherein the acetylating agent is acetic anhydride.

5. The process according to claim 1, wherein the molar ratio of base to 2-amino-6-halogenopurine ranges from 1:1 to 3:1.

6. The process according to claim 5, wherein the molar ratio of base to 2-amino-6-halogenopurine ranges from 1.5:1 to 2:1.

7. The process according to claim 1, wherein the molar ratio of acetylating agent to 2-amino-6-halogenopurine ranges from 1:1 to 3:1.

8. The process according to claim 7, wherein the molar ratio of acetylating agent to 2-amino-6-halogenopurine ranges from 1.1:1 to 2:1.

9. The process according to claim 1, wherein said treating occurs at a temperature ranging from about 1° C. to about 100° C.

10. The process according to claim 1, wherein said treating occurs for a period of time ranging from about 1 hour to about 3 hours.

11. The process according to claim 2, wherein the molar ratio of base to 2-amino-6-halogenopurine ranges from 1:1 to 3:1.

12. The process according to claim 11, wherein the molar ratio of base to 2-amino-6-halogenopurine ranges from 1.5:1 to 2:1.

13. The process according to claim 2, wherein the molar ratio of acetylating agent to 2-amino-6-halogenopurine ranges from 1:1 to 3:1.

14. The process according to claim 13, wherein the molar ratio of acetylating agent to 2-amino-6-halogenopurine ranges from 1.1:1 to 2:1.

15. The process according to claim 2, wherein said treating occurs at a temperature ranging from about 1° C. to about 100° C.

16. The process according to claim 2, wherein said treating occurs for a period of time ranging from about 1 hour to about 3 hours.

* * * * *